United States Patent [19]
Satory

[11] 3,944,018
[45] Mar. 16, 1976

[54] ACOUSTICAL SEAL

[76] Inventor: Rodney Jene Satory, 1 Wairere Road, Bellmont, Lower Hutt, Wellington, New Zealand

[22] Filed: Aug. 1, 1974

[21] Appl. No.: 493,548

[52] U.S. Cl. ............... 181/33 R; 2/209; 128/151; 179/182 R; 181/129
[51] Int. Cl.² ............................................ A42B 1/06
[58] Field of Search ....... 181/129, 33 R; 179/156 R, 179/182 R; 128/151, 152; 2/209

[56] References Cited
UNITED STATES PATENTS

| | | | |
|---|---|---|---|
| 1,365,425 | 1/1921 | Shewhart | 179/182 R |
| 3,506,980 | 4/1970 | Aileo | 2/209 |
| 3,506,981 | 4/1970 | Stewart et al. | 2/209 |
| 3,593,341 | 7/1971 | Aileo | 2/209 |

*Primary Examiner*—Stephen J. Tomsky
*Attorney, Agent, or Firm*—Henderson & Strom

[57] ABSTRACT

An acoustical ear muff arrangement having an identical acoustical sealing muff for each ear, the muffs being connected together by an adjustable spring wire structure for holding a muff over each ear. Each muff has a dish-shaped portion with elastomeric foamed material therein, and with a novel non-foamed elastomeric seal around the periphery of the dish-shaped portion. The non-foamed elastomeric seal has three lips extending from a base section. The lips have a tapering configuration and extend at angles within a critical range from the base section.

14 Claims, 4 Drawing Figures

ACOUSTICAL SEAL

BACKGROUND OF THE INVENTION

The problem of trying to keep out sound or noise is an old one. For this reason acoustical seals have been used in a variety of circumstances when it is desired that the noise level in one enclosure be significantly lower than the noise level in a neighboring enclosure. Certain materials have been found to be better at keeping out sounds than others, and it is well known that the more mass of a particular material placed between one enclosure and another, the more the sound will be kept out. Normally, there must be access to the enclosure having the low sound level, and it is for this reason that there must be seams or cracks which further need to be acoustically sealed. This too is a well known problem as evidenced by the prior art. For example, see U.S. Pat. Nos. 1,365,425; 3,506,981; and 3,593,341. While much work has been done to solve this problem, the problem has heretofore never been solved completely and satisfactorily.

The general type of device shown in the above noted patents is in the form of an enclosure known as an ear muff. It is well known that the hearing of people working in a noisy environment can easily be damaged, and it is common to wear ear muffs to reduce the sound level to which the ear itself is subject. An ear muff, generally, is a dish of solid material shaped so as to cover completely at least one ear and to press at its open edge on the face around the ear. The muff can relatively easily be made such that the reduction of noise through the material of the muff itself is satisfactory to keep out a very high proportion of any noise, but it is difficult to prevent noise from leaking between the edge of the muff and the face. Clearly the edge of the muff cannot be made to fit exactly to each individual face, and it has been the practice to line the edge of the muff with a spongy material such as natural rubber, or with an expanded soft plastic. If such an ear muff is pressed against the face with sufficient force, the reduction in the noise is relatively satisfactory, but the pressure on the face is normally too high for comfort. This discomfort is intensified if the wearer of the ear muffs wears glasses or spectacles. Alternatively, the edge of the ear muff has been lined with an oil-filled flexible material, but this too, because of the pressure required, can be uncomfortable when pressed against the face, it is quite expensive and additionally it sometimes leaks.

SUMMARY OF THE INVENTION

The present invention relates to a novel acoustical seal having a base section and three tapering lips formed of a nonfoamed elastomeric material extending from the base section on one side thereof. The two outer lips are spaced from each other, but extended generally the same somewhat outwardly direction, the outermost lip being the longest of the three. The inner lip extends in a somewhat inwardly direction about the same distance as the middle lip extends outwardly. The base section lies generally in a plane, and the three lips respectively each form an acute angle which is in the critical range of 45° to 65° from the plane.

An object of the present invention is to provide an improved acoustical seal.

Another object is to provide an acoustical seal which will adapt to an irregular surface such as a face and which will still seal without requiring a large force thereon.

A further object of the invention is to provide an acoustical seal which has several sound reflecting walls and several sound filtering air compartments.

Still another object of the invention is to provide an acoustical seal which is versatile enough to function in various devices from a seal on an ear muff to a seal around a door to a room.

Other objects, advantages, and novel features of the present invention will become apparent from the following detailed description of the invention when considered in conjunction with the accompanying drawings.

DESCRIPTION OF THE PREFERRED EMBODIMENT

Figure 1:
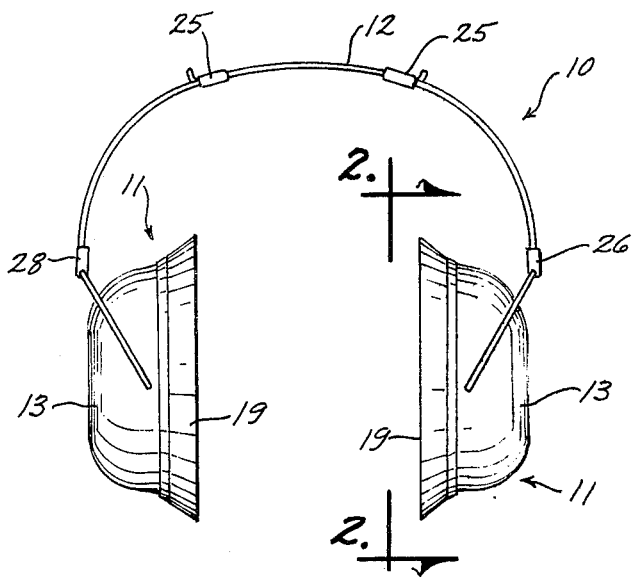
FIG. 1 shows a side view of a preferred embodiment of the present invention.
Figure 2:
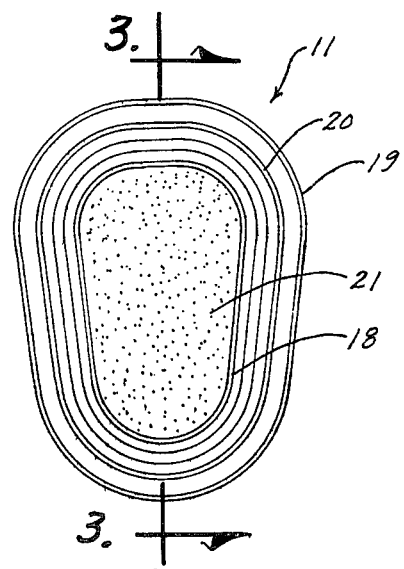
FIG. 2 shows a view of one of the ear muffs of FIG. 1 taken along line 2—2 of FIG. 1.

Referring now to the drawings wherein like reference numerals designate identical or corresponding parts throughout the several views, a preferred embodiment of the present invention to an acoustical seal is shown. FIG. 1 shows an ear muff arrangement having two identical ear muffs 11 connected together by a spring wire structure 12. The spring wire structure 12 provides a slight force to force the muffs 11 around a person's ears and against a person's head for filtering out unwanted or excessive noises.

Figure 3:
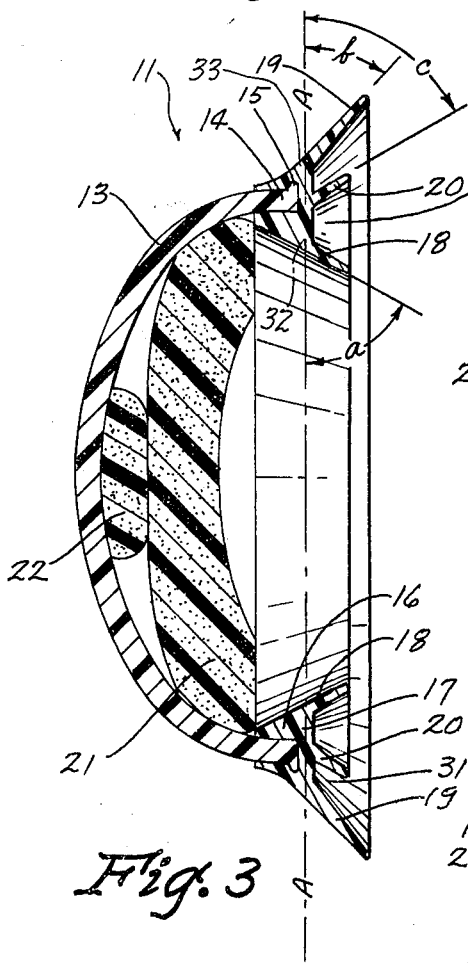
FIG. 3 is a cross sectional view of an ear muff taken along line 3—3 of FIG. 2.

FIG. 3 best shows the dish-shaped member 13 of the muff 11. The dish-shaped member 13 is formed of a rigid material such as a hard plasticized material. The peripheral edge 14 of the dish-shaped member 13 has a projecting edge 15 therearound, the purpose of which will be explained below. Connected to the peripheral edge 14 of the dish-shaped member 13 is an acoustical seal 16. The acoustical seal 16 has a groove in one side thereof which is of a complementary shape to that of the peripheral edge 14 of the dish-shaped member 13. Consequently, the acoustical seal 16 may be forced over the peripheral edge 14 of the dish-shaped member 13 and is held in that position because of the configuration of the projecting ridge 15 on the peripheral edge 14.

The acoustical seal 16 has a base section 17 which is generally defined by the plane A—A. The above discussed portion of the acoustical seal 16 which connects to the peripheral edge 14 of the dish-shaped member 13 is on one side of plane A—A, as seen in FIG. 3, and first, second and third lips 18, 19 and 20 respectively extend on the other side of the base member 17.

The acoustical seal 16 is formed of elastomeric material such as plasticized PVC, or other material having similar characteristics. Foamed material such as foam rubber or foamed plastic is not, however, suitable for the material of acoustical seal 16.

The first annular rib 18 is connected to the inner periphery 32 of the base section 17, and projects inwardly and on the right side of the plane A—A as shown in FIG. 3 at an angle a from plane A—A. The second annular rib 19 is connected to the outer periphery 33 of the base section 17 and extends outwardly and to the right side of plane A—A at an angle b, as shown in FIG. 3. The third annular lip 20 extends outwardly and to one side of the plane A-A of base section 17 at an angle c from plane A—A.

As can be seen from FIG. 3 of the drawings, the annular lips 18, 19 and 20 are thin, and taper from a slightly wider base to a narrower end portion. It is important to utilize rather thin lips on the present invention rather than the wider lips as shown in the prior art. The length of first and third annular lips 18 and 20 should be at least three times their average thickness, while the length of the outer annular lip 19 should be at least five times its average thickness, as seen in FIG. 3.

In the preferred embodiment of the invention angle a would be 60°, angle b would be 45°, and angle c would be 60°. While these angles may vary somewhat from these specific degrees, it has been found that the angles a, b and c must be within a range of 45° to 65° from the plane A-A of the base section 17 in order for the acoustical seal of the present invention to function in an optimum manner.

Also associated with the ear muff 11 is a foamed elastomeric material inside of the dish-shaped member 13, as shown by the large foamed elastomeric member 21 and the small foamed elastomeric member 22 as best seen in FIG. 3. Members 21 and 22 tend to help prevent any sounds from coming directly through the dish-shaped member 13, while the acoustical seal 16 forms a seal between the dish-shaped member 13 and the side of a person's head, surrounding the person's ear.

Figure 4:
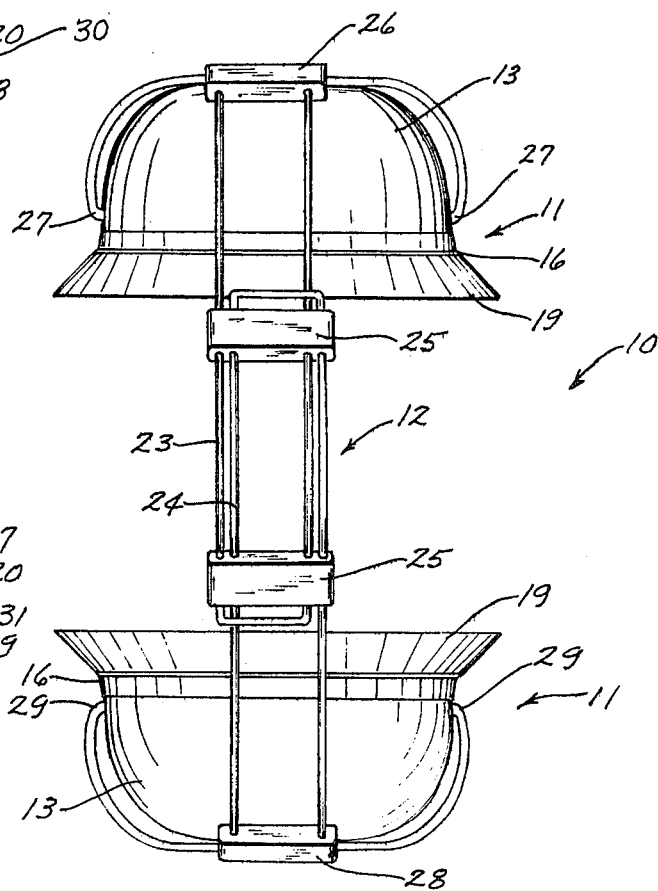
FIG. 4 is a top view of the ear muff arrangement shown in FIG. 1.

FIG. 4 better shows the construction of the spring wire connecting device 12 which is basically formed of two pieces of wire 23 and 24, each of which is associated with a respective one of the ear muffs 11. The wires 23 and 24 are connected together by plastic members 25. The wires 23 and 24 are slidable within the plastic members 25 to form a sliding joint which may be adjusted to regulate the pressure on a person's head and is also adaptable to be sized for various sizes and shapes of heads. Another plastic member 26 is associated with the wire portion 23 and helps keep the ends 27 of the wire 23 inside of holes in the dish-shaped member 13. The holes in the dish-shaped member 13 receive the ends 27 of the spring wire 23. Similar structure is associated with the spring wire 24 as indicated by plastic member 28 and end portions 29.

When the muff 11 is placed against a surface such as a person's head and around a person's ear, a first air compartment 30 is formed between lips 18 and 20, and a second air compartment 31 is formed between the annular lips 19 and 20. Consequently, sound must pass through both compartments 30 and 31, and also through each of the lips 18, 19 and 20 in order to get through the acoustical seal 16 and into the inner part of the dish 13 of the muff 11. It has been found that very little pressure is needed to form this seal against the head.

Tests have been conducted on a seal constructed as shown in the drawings and it was found that the reduction in sound was greater than 30 decibels at all frequencies over 250 Hz when pressed with a pressure of about 200 g. Comparative tests were made against an ear muff equipped with conventional sponge edges, and it was found the the acoustical resistence of the two patterns was approximately the same if the seal of the present invention was subjected to 200 g and sponge seal was subjected to 600 g of pressure. It can therefore be seen that the present invention accomplishes all of the objects mentioned above.

Obviously many modifications and variations of the present invention are possible in light of the above teachings. It is therefore to be understood that, within the scope of the appended claims, the invention may be practiced otherwise than as specifically described.

I claim:
1. An acoustical seal comprising:
an annular base lying generally in a first plane and having an inner and an outer periphery thereon;
a first annular elastomeric lip connected to said inner periphery and extending inwardly and to one side of said plane at a first acute angle of between 45° and 65° with respect to said plane;
a second annular elastomeric lip connected to said outer periphery and extending outwardly and to said one side of said plane at a second acute angle of between 45° and 65° with respect to said plane;
a third annular elastomeric lip connected to said base between said first and second lips and extending outwardly and to one side of said plane at a third acute angle of between 45° and 65° with respect to said plane; and
annular means attached to said base on the other side of said plane for acoustically sealing said base to a closure member.

2. An acoustical seal as defined in claim 1 wherein said second lip extends further to said one side of the plane than does said first lip.

3. An acoustical seal as defined in claim 2 wherein the second acute angle of said second lip is 45° and the first and third acute angles of said first and third lips respectively are 60°.

4. Apparatus as defined in claim 1
wherein said closure member is dish-shaped and has a peripheral edge;
said base member being sealingly attached to said peripheral edge.

5. Apparatus as defined in claim 4 wherein a foamed elastomeric mass is disposed within said dish-shaped closure member.

6. Apparatus as defined in claim 5 including means for holding said acoustical seal in abutment with a person's head and surrounding the person's ear to thereby prevent the transmission of noise to the ear.

7. Apparatus as defined in claim 4 wherein said annular means includes an annular groove, said peripheral edge being received in said annular groove.

8. Apparatus as defined in claim 7 wherein said peripheral edge includes a radially outwardly projecting ridge.

9. An acoustical seal as defined in claim 1 wherein said acoustical seal is contructed of a non-foamed elastomeric material.

10. An acoustical seal as defined in claim 1 wherein a first air space is formed between said first and third lips and a second air space is formed between said second and third lips, said first and second air spaces being void of anything other than air.

11. An acoustical seal as defined in claim 1 wherein said first, second and third lips have a tapering configuration, being thicker near the connection to the base than at the free ends thereof.

12. An acoustical seal as defined in claim 11 wherein said first and third annular lips have a length which is at least three times the average thickness thereof and said second annular lip has a length of at least five times the average thickness thereof.

13. The acoustical seal as defined in claim 1 wherein said acoustical seal is of one piece solid construction.

14. The acoustical seal as defined in claim 13 wherein said acoustical seal in constructed of polyvinylchloride substantially free of confined air pockets.

* * * * *